United States Patent
Kroener

(10) Patent No.: US 9,389,200 B2
(45) Date of Patent: Jul. 12, 2016

(54) SENSOR DEVICE, A METHOD AND A SENSOR TO DETERMINE A RELATIVE CONCENTRATION OF A FIRST KIND OF IONS WITH RESPECT TO A SECOND KIND OF IONS SOLUTE IN A DROP OF LIQUID

(71) Applicant: Infineon Technologies AG, Neubiberg (DE)

(72) Inventor: Friedrich Kroener, Villach (AT)

(73) Assignee: Infineon Technologies AG, Neubiberg (DE)

(*) Notice: Subject to any disclaimer, the term of this patent is extended or adjusted under 35 U.S.C. 154(b) by 314 days.

(21) Appl. No.: 13/673,392

(22) Filed: Nov. 9, 2012

(65) Prior Publication Data
US 2014/0131224 A1    May 15, 2014

(51) Int. Cl.
| G01N 27/414 | (2006.01) |
| G01N 27/49 | (2006.01) |
| G01N 27/48 | (2006.01) |

(52) U.S. Cl.
CPC ............. *G01N 27/49* (2013.01); *G01N 27/414* (2013.01); *G01N 27/4145* (2013.01); *G01N 27/48* (2013.01)

(58) Field of Classification Search
CPC ..... G01N 27/48; G01N 27/49; G01N 27/414; G01N 27/4145
USPC ................. 205/789, 789.5; 204/403.01, 416
See application file for complete search history.

(56) References Cited

U.S. PATENT DOCUMENTS

| 3,556,950 | A | | 1/1971 | Dahms |
| 3,840,438 | A | | 10/1974 | Ast et al. |
| 4,874,499 | A | * | 10/1989 | Smith et al. ............. 204/403.03 |
| 5,102,526 | A | | 4/1992 | Brown et al. |
| 5,126,034 | A | * | 6/1992 | Carter et al. ............ 204/403.05 |
| 5,602,467 | A | | 2/1997 | Krauss et al. |
| 6,682,649 | B1 | * | 1/2004 | Hansen et al. ............. 205/777.5 |
| 7,799,204 | B2 | | 9/2010 | Zhang et al. |
| 2004/0071598 | A1 | | 4/2004 | Hower et al. |
| 2007/0138027 | A1 | * | 6/2007 | Dinsmoor et al. ......... 205/787.5 |
| 2007/0241068 | A1 | * | 10/2007 | Pamula et al. ................ 210/806 |
| 2008/0011606 | A1 | | 1/2008 | Zhang et al. |
| 2009/0239033 | A1 | * | 9/2009 | Nakatani et al. .............. 428/137 |
| 2009/0301876 | A1 | * | 12/2009 | Wagner et al. ................ 204/415 |
| 2010/0051552 | A1 | | 3/2010 | Rohde et al. |

FOREIGN PATENT DOCUMENTS

| DE | 4228609 C1 | 1/1994 |
| DE | 4406908 A1 | 9/1995 |
| GB | 1346532 A | 2/1974 |
| WO | 2006040588 A1 | 4/2006 |

* cited by examiner

*Primary Examiner* — Luan Van
*Assistant Examiner* — Steven Rosenwald
(74) *Attorney, Agent, or Firm* — Eschweiler & Associates, LLC

(57) ABSTRACT

A sensor device according to an embodiment includes a semiconductor substrate including a plurality of channels, the channels connecting a cavity and a measurement electrode, and a counter electrode arranged to be in contact with the cavity, wherein the cavity, the measurement electrode and the counter electrode are arranged to accommodate a drop of a liquid and to allow a voltage to be applied to the drop of liquid.

24 Claims, 4 Drawing Sheets

SENSOR DEVICE, A METHOD AND A SENSOR TO DETERMINE A RELATIVE CONCENTRATION OF A FIRST KIND OF IONS WITH RESPECT TO A SECOND KIND OF IONS SOLUTE IN A DROP OF LIQUID

FIELD

Embodiments relate to a sensor device, a method to determine a relative concentration of a first kind of ions with respect to a second kind of ions solute in a drop of liquid, a sensor for determining a relative concentration of a first kind of ions with respect to a second kind of ions solute in a drop of liquid, a sensor for determining a relative concentration of potassium ions ($K^+$) with respect to sodium ions ($Na^+$) solute in a drop of blood and a computer program having a program code for performing an embodiment of such a method.

BACKGROUND

In many fields of applications, a concentration of a chemical substance is to be determined. Such applications come, for instance, from the fields of analytics, environmental technology and medical applications. In many cases, these analyses are carried out under field conditions outside a laboratory or a similar environment. Simple usability is, therefore, often a desired design goal.

Depending on the nature of the analysis, its circumstances and further boundary conditions, the sensor device coming into contact with the substance to be analyzed may, eventually, not be usable again. This may be caused by a degradation of the sensor device, a contamination of the sensor device or for other reasons, for instance, in medical application for hygienic reasons. Therefore, it may be interesting to design the sensor device in such a way that it is easy to replace. Therefore, an efficient fabrication might also be interesting.

Therefore, a demand exists to improve a trade-off between an efficient fabrication, an accurate determination of a concentration and a simple usability.

SUMMARY

A sensor device according to an embodiment comprises a semiconductor substrate comprising a plurality of channels, wherein the channels connect the cavity and the measurement electrode. The sensor device further comprises a counter electrode arranged to be in contact with a cavity, wherein the cavity, the measurement electrode and the counter electrode are arranged to accommodate a drop of liquid and allow a voltage to be applied to the drop of liquid.

A method according to an embodiment to determine a relative concentration of a first kind of ions with respect to a second kind of ions solute in a drop of liquid comprises providing a voltage to a measurement electrode and a counter electrode, wherein the measurement electrode is provided to a semiconductor substrate comprising a plurality of channels. The channels connect the cavity and the measurement electrode, wherein the counter electrode is arranged to be in contact with a cavity. The cavity, the measurement electrode and the counter electrode are, arranged to accommodate the drop of liquid and to allow a voltage to be applied to the drop of liquid. The method further comprises determining a current or a change of the current flowing through the drop of liquid in response to the voltage applied and providing an evaluation signal indicative of the relative concentration based on the determined current or the determined change of the current.

Embodiments are based on the finding that a trade-off between an efficient fabrication, an accurate determination of a concentration and a simple usability may be improved by providing the semiconductor substrate comprising the plurality of channels between the cavity, which is arranged to accommodate the drop of liquid, and the measurement electrode, to which at least partially a voltage can be applied. Due to this arrangement, the semiconductor substrate with the plurality of channels efficiently restricts the number of ions reaching the measurement electrode allowing—despite only using a drop of liquid—controlled measurement conditions to allow a determination of the relative concentration of the first and second kinds of ions with respect to each other. Moreover, the semiconductor substrate with the plurality of channels can efficiently be fabricated. As a consequence, the sensor device may eventually be easily replaceable and therefore allow an easier handling thereof.

BRIEF DESCRIPTION OF THE DRAWINGS

Several embodiments of the present invention will be described in the enclosed FIGS.

DETAILED DESCRIPTION

Figure 1:
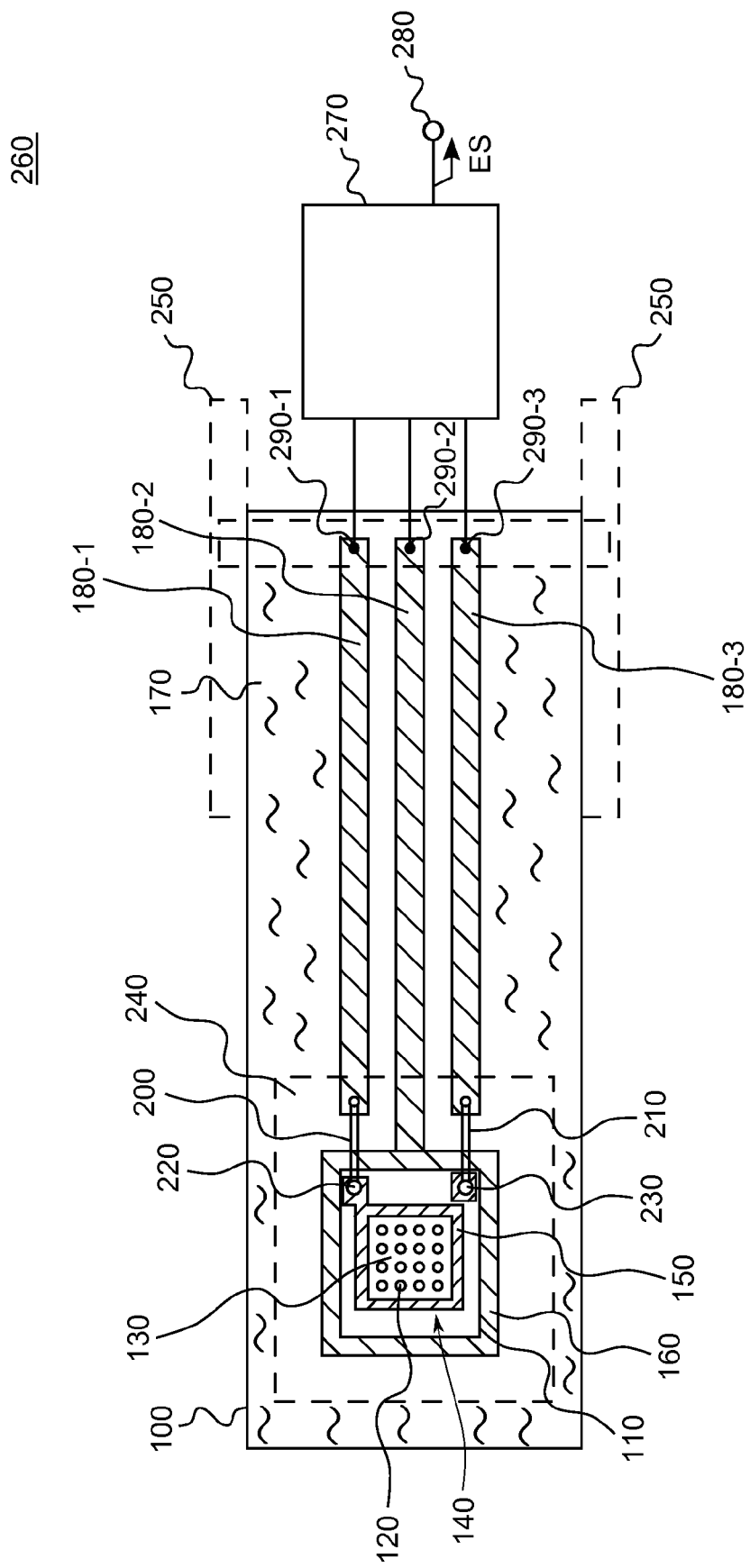
FIG. 1 shows a plan view of a sensor device according to an embodiment.

In the following, embodiments according to the present invention will be described in more detail. In this context, summarizing reference signs will be used to describe several objects simultaneously or to describe common features, dimensions, characteristics, or the like of these objects. The summarizing reference signs are based on their individual reference signs. Moreover, objects appearing in several embodiments or several figures, but which are identical or at least similar in terms of at least some of their functions or structural features, will be denoted with the same or similar reference signs. To avoid unnecessary repetitions, parts of the description referring to such objects also relate to the corresponding objects of the different embodiments or the different figures, unless explicitly or—taking the context of the description and the figures into account—implicitly stated otherwise. Therefore, similar or related objects may be implemented with at least some identical or similar features, dimensions, and characteristics, but may be also implemented with differing properties.

In many fields of applications, a determination of the concentration of a chemical substance, such as a specific kind of ion, in an aqueous or non-aqueous solution, is to be determined. Especially in the case of an analysis of an extremely small sample volume with very low concentrations of the respective ions, this may pose an additional challenge. One such example comes from an analysis of a drop of blood with respect to its potassium concentration based on a cheap analysis method to enable a person endangered of a heart attack to monitor his or her condition back home.

Conventionally, measurements of special ion concentrations by means of electrochemical systems often utilizes reference electrodes, a calibration standard or other auxiliary systems to achieve the necessary precision. Due to these additional structures and the effort connected thereto, these systems are typically capable of providing accurate absolute values concerning the respective concentration values. However, these systems are not very suitable for, for instance, monitoring back home the potassium values of a patient's blood.

However, by concentrating on a ratio of the potassium level to another kind of ions, monitoring and determining the concentration of potassium ions with respect to another, second kind of ions solute in a drop of blood can be determined using a single chip sensor device as will be described below.

However, embodiments are not limited to measuring potassium levels of a drop of blood, but may be used in the context of measuring all kinds of concentrations of a first kind of ion solute in a drop of a liquid. The liquid may be an aqueous or a non-aqueous solution of the first kind of ions. Based on a single sensor device according to an embodiment, a determination of a relative concentration of the first kind of ions with respect to a second kind of ions solute in the drop of liquid can be achieved. However, for the sake of simplicity, in the following, embodiments of a sensor device, a sensor and a method to determine the relative concentration of the first kind of ions with respect to the second kind of ions will be described in the context of a determination of potassium ions ($K^+$) with respect to sodium ions ($Na^+$) as one example.

A sensor device according to an embodiment may, for instance, be based on a microprobe fabricated in MEMS-technology (MEMS=Micro-Electro-Mechanical-System) capable of determining a concentration difference of different ions in an aqueous or non-aqueous solution, especially of metallic ions by measuring the concentration based on cyclic voltammetry.

Figure 2:
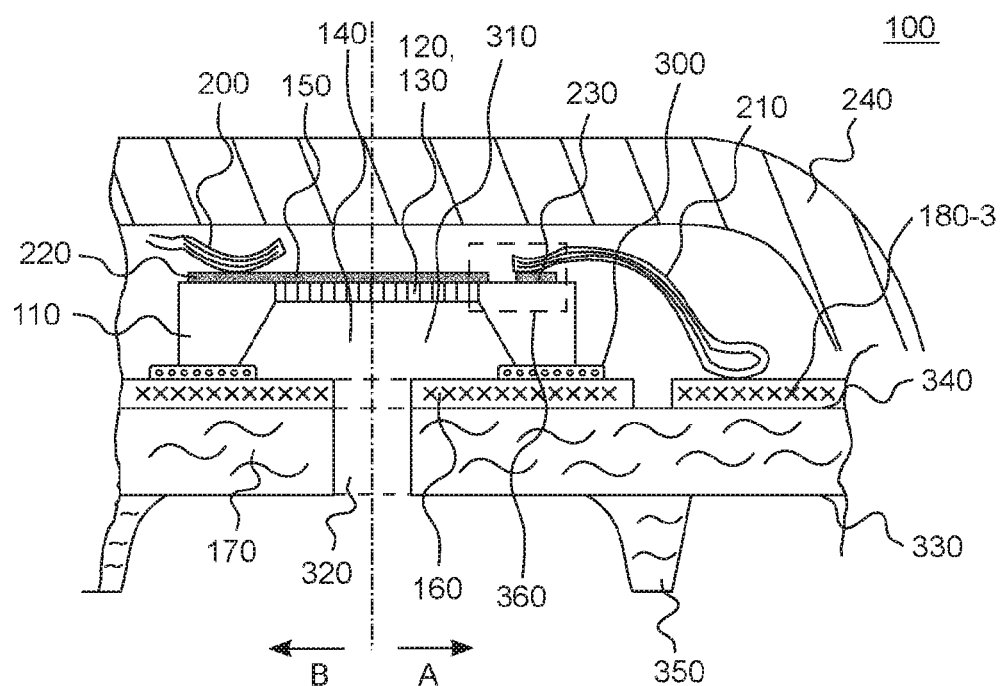
FIG. 2 shows a cross-sectional view through the sensor device of FIG. 1.
Figure 3:
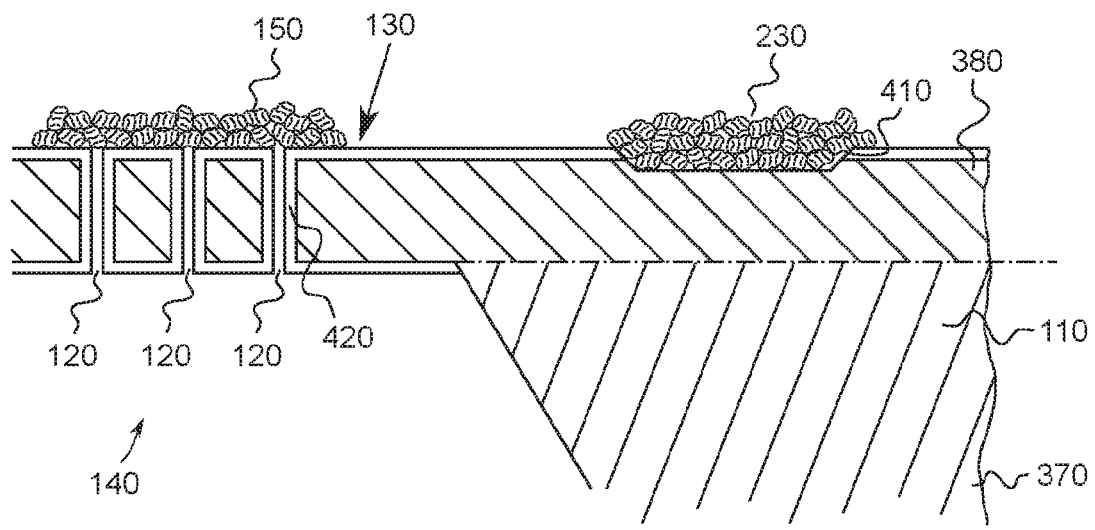
FIG. 3 shows an enlarged portion of a cross-sectional view of FIG. 2.

FIGS. 1, 2 and 3 show a plan view, a cross-sectional view and an enlarged portion of the cross-sectional view, respectively, of a sensor device 100 according to an embodiment. As shown in FIG. 1, the sensor device 100 comprises a substrate 110 comprising a plurality of channels 120, a fraction of which are shown, but not drawn to scale in FIG. 1. The substrate 110 may be a semiconductor substrate, for instance, a silicon substrate (Si), a gallium-arsenide substrate (GaAs) or any other semiconductor substrate. The channels 120 are arranged in a membrane section 130, which is also referred to as the membrane. The channels 120 separate a cavity 140 from a measurement electrode 150. The membrane section 130 typically comprises a smaller thickness of the substrate 110 perpendicular to the main surface of the substrate 110 compared to another region, for instance the region of the bond pads 220, 230.

The sensor device 100 further comprises a counter electrode 160 which is arranged to be in contact with a cavity 140. The cavity 140, the measurement electrode 150 and the counter electrode 160 are furthermore arranged in such a way that the cavity is capable of accommodating a drop of the liquid to be analyzed and to allow a measurement voltage to be applied to the drop of liquid inside the cavity.

The sensor device 100 further comprises a carrier 170, which may, for instance, be fabricated as a printed circuit board (PCB) to which the substrate 110 is mechanically fixed such that the cavity 140 is formed between the membrane section 130 and the carrier 170. In other words, the cavity 130 is formed between the plurality of channels 120 and the carrier 170.

As will be laid out in more detail below, the counter electrode 160 is also provided on the carrier 170. The carrier 170 also comprises a plurality of electrical contacts 180-1, 180-2 and 180-3, which are electrically coupled to the measurement electrode 150, the counter electrode 160 and a control electrode 380. While the electrical contact 180-2 for the counter electrode 160 disposed on the carrier 170 is directly fabricated onto the carrier 170, for instance, by a screen printing process integrally forming the counter electrode 160 and the electrical contact 180-2. The electrical contacts 180-2, 180-3 of the measurement electrode 150 and the control electrode 380, respectively, are formed by electrical bonds 200, 210, respectively, connecting the electrical contacts 180-2, 180-3 and corresponding bond pads 220, 230, respectively, deposited and patterned on the substrate 110. In the embodiment shown in FIG. 1, the bond pads 220, 230 are formed outside the membrane section 130 comprising the channels 120.

However, to enable an electrical contact between the bond pad 220 and the measurement electrode 150, both are electrically coupled and, for instance, integrally formed by the corresponding deposition of a conductive material such as a metal (e.g. aluminum (Al), copper (Cu), gold (Au), silver (Ag)) and one or more corresponding patterning steps as will be laid out below.

Optionally, the sensor device 100 may further comprise a protective cover 240, which may be, for instance, formed of a polymer. The protective cover 240 may be configured to protect the substrate 110, the electrical bonds 200, 210 and, therefore, at least parts of the electrical contacts 180.

The carrier 170 is further adapted to allow it to be mechanically mounted into a holder 250 of a sensor 260 according to an embodiment. The sensor 260 further comprises an evaluation circuit 270 which is electrically coupled to the electrical contacts 180. As will be laid out in more detail below, the evaluation circuit 270 is therefore adapted to provide the voltage or measurement voltage to the measurement electrode 150 and the counter electrode 160 by applying a measurement potential to the measurement electrode 150 and a reference potential to the counter electrode 160. A difference between the measurement potential and the reference potential is equal to the measurement voltage applied to the mentioned electrodes 150, 160.

The evaluation circuit 270 is further configured to determine a current or a change of the current flowing through the drop of liquid provided to the cavity 140 in response to the applied voltage. Based on the determined current or the determined change of the current in response to the applied voltage, the evaluation circuit 270 is further configured to provide an evaluation signal ES indicative of the relative concentration of the first and second kinds of ions solute in the drop of liquid at an optional terminal 280 of the evaluation circuit 270. To apply the voltage to the measurement electrode 150 and the counter electrode 160, the sensor 100 comprises a corresponding number of counter electrical contacts 290-1, 290-2, 290-3, which are adapted to electrically couple the electrical contacts 180-1, 180-2, 180-3, respectively, to the evaluation circuit 270, when the sensor device 100 is mounted to the holder 250. The counter electrode contacts 290 may, for instance, comprise spring contacts or other suitable contact structures.

By means of the holder 250, the sensor device 100 can be mounted to and dismounted from the sensor 260. As a consequence, the sensor device 100 can easily by exchanged, even under field conditions outside a laboratory, a practice, a hospital or a similar controlled environment. Therefore, the sensor 260 and the sensor device 100 according to embodiments may provide the opportunity to determine the relative concentration of the first and second kinds of ions with respect to each other in the drop of a liquid even under non-optimal conditions. In the medical field of application, the sensor device 100 along with the sensor 260 may, for instance, be used to analyze the potassium ion ($K^+$) concentration with respect to the sodium ion ($Na^+$) concentration in a drop of blood by a patient. For instance, when the concentration of the potassium ions rises above a threshold with respect to the concentration of the sodium ions, for instance, above a value of 2% to 3%, this may indicate a medical condition of the heart of the patient requiring medical attention. In other words, in the medical section, a sensor 260 may be used to indicate to a person suffering from a heart condition to seek medical consultation.

In other words, onto the strip-shaped carrier 170 as shown in FIG. 1, three electrical contacts 180 are printed in the form of conductive paths to allow the sensor device 100 to be brought into contact with an external device such as a sensor 260 comprising the previously mentioned holder 250 along with the evaluation circuit 270. As laid out earlier, the carrier 170 may be fabricated from the material of a printed circuit board.

FIG. 2 shows a cross-sectional view of a sensor device 100 along two planes A and B. The plane A extends along the electrical contact 180-3 and a direction perpendicular to the main surface of the substrate 110. Plane B extends in parallel to plane A, but extends along the electrical contact 180-1. As a consequence, on the right side of FIG. 2 (cross-section plane A), the electrical contact 180-3 of the control electrode 380 (not shown in FIG. 2) is shown along with the electrical bond 210 and the corresponding bond pad 230 electrically coupling the control electrode 380 to its electrical contact 180-3. Moreover, FIG. 2 shows in its right part, the counter electrode 160 deposited onto the carrier 170. The substrate 110 is mechanically fixed to the carrier 170 by an adhesion 300.

The substrate 110 comprises the previously-mentioned membrane section 130 in the area of which the thickness of the substrate 110 is significantly smaller than in the outside areas on which the bond pads 220, 230, for electrically connecting the control electrode 380 (not shown in FIG. 2) and the measurement electrode 150 are deposited. The bond pad 220 for the electrical bond 200 coupling the measurement electrode 150 to the electrical contact 180-1 is shown in the left part of FIG. 2 in the cross-sectional plane B.

In other words, the cavity 140 is formed by a recess 310 patterned onto a back side of the substrate 110 in the area of the membrane section 130. As previously mentioned, the membrane section 130 comprises the plurality of channels 120 extending essentially perpendicular to the main surface of the substrate 110.

To enable the user of the sensor device 100 to provide the drop of liquid into the cavity 140, the carrier 170 further comprises a hole 320 to allow the drop of liquid to be provided to the cavity 140. The hole 320 extends completely through the carrier 170 interconnecting a back side 330 of a carrier and a fore or top side 340 onto which the electrical contacts 180 and the substrate 110 are provided. The sensor device 100 further comprises a funnel 350 which is mechanically fixed around the hole 320 on the carrier 170 on the back side 330 of the carrier 170. In other words, the funnel 350 is provided to the far side of the semiconductor substrate 110. The funnel 350 may, for instance, be fabricated from any plastic material, such as a glass-fiber reinforced plastic material (GRP=Glass-fiber Reinforced Plastic). The funnel 350 may, for instance, be adhesively coupled to the back side 330 of the substrate 110 by an epoxy.

In the case of a sensor device 100 configured to be used to determine the ion concentrations in a drop of blood, the funnel 350 may, for instance, have a diameter of several millimeters, for instance of more than 4, 6 or 10 mm. In contrast, the diameter of the hole 320 is typically smaller and, for instance, may be in the range of 3 mm or below. For instance, the hole 320 may have a diameter of 2 mm.

As described before, the sensor device 100 comprises the protective cover 240 covering not only the substrate 110 and the cavity 140 but also the electrical contacts, especially the electrical bonds 200, 210.

FIG. 3 shows an enlarged portion of the cross-sectional view of FIG. 2 depicted in FIG. 2 by a box 360. However, the enlarged portion shown in FIG. 3 indicated by a box 360 in FIG. 2 is not drawn to scale and the electrical bond 210 interconnecting the bond pads 230 to the electrical contact 180-3 is not shown.

The substrate 110 comprises a first section 370, which, for instance, may be identical in terms of its electrical and doping characteristics to the substrate material of the substrate 110 prior to the fabrication of the sensor device 100. For instance, the first section 370 may comprise a hole-doped silicone material (p-Si). Adjacent to the first section 370 the substrate 110 further comprises a second section 380, which may, for instance, comprise a highly-doped layer of the opposite doping compared to the first section 370. In other words, if the first section 370 is a hole-doped or p-doped silicon material, the second section 380 may comprise an electron-doped or n-doped silicone material. The second section 380 also forms in the embodiment shown in FIGS. 1 to 3, the membrane section 130 comprising the plurality of channels 120, three of which are shown in FIG. 3.

The measurement electrode 150 is deposited on the surface of the substrate 110 and its membrane section 130 facing away from the cavity 140. Accordingly, the channels 120 separate the measurement electrode 150 from the cavity 140 to which the drop of liquid can be applied.

The channels 120 typically comprise a characteristic width, for instance, a characteristic diameter perpendicular to an extension of the channels 120 between the measurement electrode 150 and the cavity 140 of up to 1 μm. In other embodiments, the characteristic width perpendicular to the extension of the channels 120 may be smaller, for instance, not more than 700 nm, not more than 500 nm, not more than 200 nm or not more than 100 nm. As a consequence, the channels 120 prevent colloids, blood cells and other large particles from reaching the measurement electrode 150.

To electrically insulate the measurement electrode 150 from the second section 380 of the substrate 110, the substrate 110 is covered at least in the area of the measurement electrode 150 by an insulating layer 420. The insulating layer 420 may, for instance, be formed by at least one of an oxide or a nitride material.

As outlined before, the second section 380 of the substrate 110 comprises an electrically conducting material. In other words, the substrate 110 comprises an electrically conductive region 400 insulated from the channels 120. The electrically conductive region 400 is furthermore adapted to apply a control potential to the drop of liquid inside the cavity 140. To enable this, the insulating layer 420 on top of the substrate 110 comprises in the area of the bond pad 230, at least partially an opening 410 electrically coupling the bond pad 230 to the second section 380 and, therefore, to the electrically conducting region 400.

To prevent the electrically conductive region from exchanging charge carriers with the drop of fluid, an insulating region 420 abutting the electrically conductive region and the channels 120 is arranged in between the electrically conductive region and the channels 120. As a consequence, the electrically conductive region and the insulating region 420 are adapted to apply a control potential to the drop of the liquid. The electrically conductive region is therefore also referred to as a gate electrode.

The insulating layer 420 and the insulating region 420 may be integrally formed, for instance, in the same fabrication step. Therefore, in some embodiments of a sensor device 100, the insulating region 420 may be considered to comprise the insulating layer 420 or vice-versa.

For the same reasons, also the insulating region 420 may be formed by at least one of an oxide or a nitride material to insulate the electrically conductive region from the liquid. The electrically conductive region 400 may be formed by a doped region of the semiconducting material of the substrate 110. Therefore, the control electrode 380 may comprise or may be formed by the electrically conductive region 400.

Based on an area of the membrane section 130 of, for instance, 4 mm$^2$, based on a typical thickness of a substrate 110, the cavity 140 may comprise a volume of several, for instance 2 µl. In different embodiments, based on the actual thickness of the substrate 110, the area of the membrane section 130, a volume of up to 20 µl of the cavity 140 may be realized.

To analyze the concentration of, for instance, positive ions (cations) the electrical contact 180-2 may, for instance, be used as the anode of the electrochemical analysis cell formed by the sensor device 100 as described before. In other words, the counter electrode 160 will be provided with a positive potential. As a consequence, the measurement electrode 150 and its electrical contact 180-1 will be used as the cathode, while the control electrode 380 along with its electrical contact 180-3 is used as the control terminal. The measurement may, for instance, be carried out in the following manner, wherein the membrane section 130 may serve to fulfill several tasks. First of all, the membrane section may be used as a mechanical carrier for the measurement electrode 150 which may also be fabricated by screen printing or screen processing. Furthermore, the membrane section 130 provides the space for the channels 120, which prevent charged colloids and blood cells from reaching the measurement electrode 150 so that these particles will not participate to a larger extent to noise and other distortions of the signals to be analyzed. Finally, the membrane section 130 may be formed from a highly conductive n-doped silicone (n-Si) covered at the surface of the channels 120, which are also referred to as pores, with an electrical insulator forming the insulating region 420 and, therefore, forming the sometimes so-called gate oxide.

By means of the control terminal or electrical contact 180-3, and the bond pad 230 a high capacity may be formed in the area of the channels 120, which may be used to amplify the signal to be analyzed. Naturally, also the bond pad 230 as the bond pad 220 of the measurement electrode 150 may be formed by screen printing or screen processing. By applying a control potential to the control electrode 380, the difference between the at least two different kinds of ions comprised in the drop of liquid, an amplification of the difference of the respective signals may be achievable. As a consequence, the bond pads 220, 230 as well as the further electrically conducting structures associated with the measurement electrode 150 and the control electrode 380 should be electrically insulated from one another by the insulating layer 420 or the insulating region 420.

The membrane section 130 may, for instance, be fabricated from n-doped silicone, while the substrate 110 and its first section 370 may comprise p-doped silicone. The cavity 140 may, therefore, be fabricated due to the different dopings at an interface between the first and second sections 370, 380 by applying pn-etching, an electrochemical etching stop technique (ECES) or a combination thereof.

As outlined before, the sensor device 100 further comprises electrical bonds 200, 210, along with bond pads 220, 230, to enable the measurement electrode 150 and the control electrode 380 to be electrically connected. Moreover, by means of the adhesion 300 the substrate 110 is mechanically fixed to the carrier 170. The substrate 110 along with its electrical connections in the form of the electrical bonds 200, 210, is protected by the protective cover 240. On the back side of the carrier 170 facing away from the substrate 110, a funnel-like wall 350 assists the user to provide the drop of liquid to the cavity 140 and to prevent the drop of liquid from leaking away. In the case of a potassium analysis, the blood is electrically coupled to the inside of the cavity 140. It penetrates the carrier 170 via the hole 320.

As outlined before, the volume of the cavity 140 depends on the area of the membrane section 130 and the thickness of the substrate 110. For instance, in the case of a 4 mm$^2$ large membrane section 130, the cavity 140 may be designed to have a volume of about 2 µl, which approximately corresponds to a size of volume of a drop of blood.

The fabrication of the cavity 140 by etching and insulating the membrane section 130 may also be carried out based on SOI basic material (SOI=Silicone On Insulator). Such a process to fabricate a sensor device 100 as a MEMS-device for cyclic voltammetry may, for instance, comprise providing an SOI-substrate, a wafer thickness of which corresponds to the later thickness of the membrane section 130. Afterwards, the substrate may be oxidized or provided with another insulating material. Afterwards, the insulating layer may be opened and to decrease a boundary resistance (Schottky-resistance) of the membrane, the control electrode 380 may be implanted. Then, resist structures may be applied for a plasma etching process of the membrane. The structures, for instance, may be formed by a nano-imprint technique. The membrane section 130 may then be etched until the buried oxide is reached. In a next step, the measurement electrode or working electrode along with the bond pad 230 of the control electrode 380 may be patterned by, for instance, screen printing or screen processing.

Afterwards, back side lithography may be carried out to define the positions of the cavities 140 of the different sensor devices to be fabricated on a single wafer, which may then be etched in a next step. Afterwards, the membrane section 130 may be electrochemically or chemically oxidized before the individual dices or chips are separated from the wafer.

The carrier 170 may then be provided along with its printed electrical contact 180 and the hole 320. The dice or, in other words, the substrate 110, may then be adhesively coupled to the carrier 170 such that the cavity 140 is arranged above the hole 320 in the carrier 170. To realize the electrical coupling of the control electrode 380 and the measurement electrode 150, the corresponding bond pads 230, 220, respectively, will be bonded using electrical bonds 210, 200, respectively, before the substrate 110 and its vicinity is packaged by providing the protective cover 240. In a last step, the funnel 350 will be adhesively coupled, for instance by gluing using an epoxy, to the back side of the carrier 170 facing away from the substrate 110.

However, the previously-described separation processes illustrating two streams of process along which a sensor device 100 according to an embodiment may be fabricated.

Before a method according to an embodiment to determine the relative concentration of the first kind of ions with respect to the second kind of ions solute in the drop of liquid will be described in more detail, wherein, for instance, the first kind of ions may comprise potassium ions ($K^+$) and the second kind of ions may comprise sodium ions ($Na^+$) for blood being the liquid, an evaluation of the determined correct-voltage measurements or conductivity-voltage measurements carried out by the sensor 260 and its sensor device 100 will be explained in more detail. With respect to FIGS. 4 and 5, providing the evaluation signal ES indicative of the relative concentration of the respective ions will be outlined in more detail. The measurement may, for instance, be carried out based on the principle of cyclic voltammetry.

Figure 4:
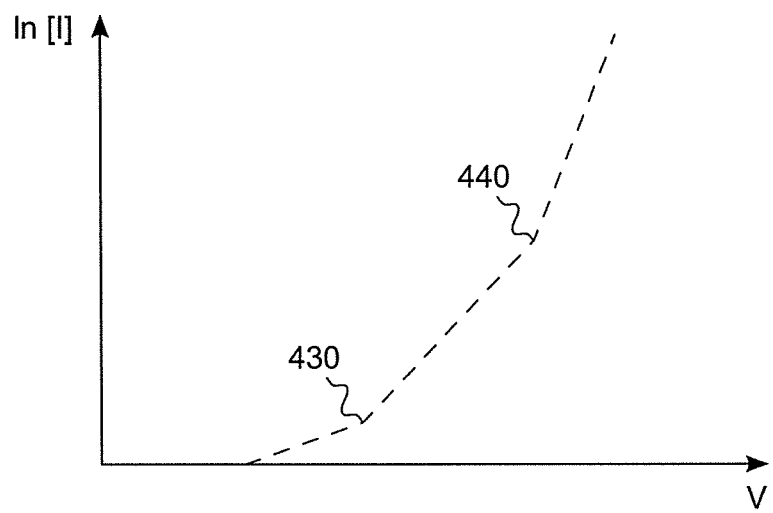
FIG. 4 illustrates a current-voltage-measurement.

FIG. 4 shows a schematic illustration of the current-voltage measurement. On the abscissa (x-axis) the voltage or measurement voltage V is plotted. On the ordinate (y-axis) the measured current I in response to the voltage V applied to the measurement electrode 150 and the reference electrode and the counter electrode 160 is plotted. To be more precise, since according to the theory of electrochemistry the observed current depends exponentially on the applied voltage, the natural logarithm ln(I) is plotted on the ordinate in FIG. 4.

The voltage V across the electrochemical cell formed by the sensor device 100 and its cavity 140 may, for instance, be continuously increased during a determination cycle during which the current I is determined. Whenever the voltage V reaches a threshold of an electrochemical reaction, the current I will increase, as indicated at a first kink 430 and a second kink 440 for two different kinds of ions. For instance, in the case of sodium, the electrochemical reaction

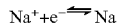

starts at around −2.71 V. Accordingly, in the case of potassium the chemical reaction

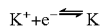

starts at about −2.931 V. As a consequence, the measurement indicated in FIG. 4 shows an example of a measurement comprising two kinks 430, 440, the positions and/or magnitudes of which can be compared to obtain information regarding the relative concentration of the potassium ions with respect to the sodium ions or vice-versa.

Figure 5:
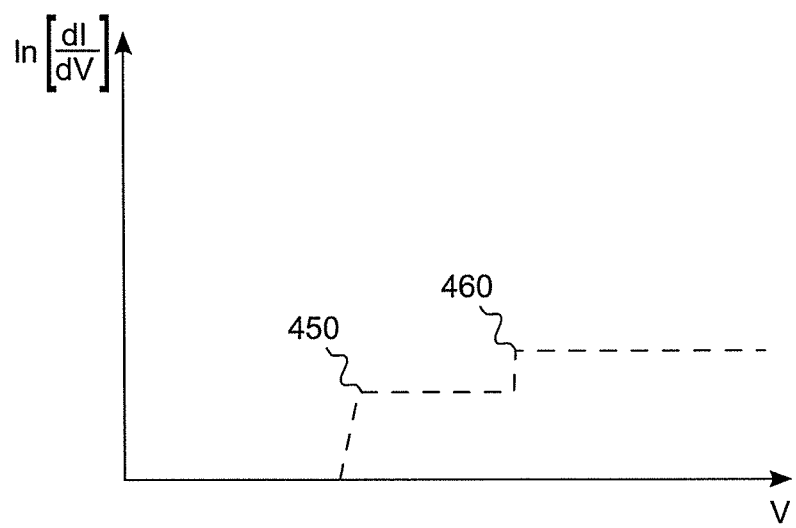
FIG. 5 illustrates a conductivity-voltage-measurement.

FIG. 5 shows a conductivity-voltage measurement. The conductivity dI/dV is given as the slope of the current-voltage measurement or, in other words, as the derivative of the current I with respect to the voltage V. Once again, on the ordinate of the diagram in FIG. 5, the natural logarithm of the conductivity ln(dI/dV) is plotted instead of the conductivity dI/dV as outlined in the context of FIG. 4.

The conductivity-voltage measurement of FIG. 5 corresponds to the current-voltage measurement of FIG. 4. The measurement shown in FIG. 5 can, for instance, be acquired by differentiating the measurement shown in FIG. 4. However, also the conductivity dI/dV may be directly determined or measured, for instance, using a lock-in technique.

The evaluation circuit 270 of the sensor 260 can, in principle, work based on the current-voltage measurement as shown in FIG. 4, or the conductivity-voltage measurement shown in FIG. 5: However, it may be more accurate to utilize the conductivity-voltage measurement since the kinks 430, 440 of the current-voltage measurement become steps 450, 460, which may be more easily evaluated in terms of their positions and/or difference values rather than the discontinuities in the slope of the corresponding kinks 430, 440.

By applying a control potential to the control electrode 160, thereby biasing the membrane or membrane section 130, the amount of charge accumulated inside the channels 120 before the measurement electrode 150 can be controlled. As a consequence, it may be possible to achieve a relative independence of the measurements of the ratio of the different kinds of ions of the respective diffusion constants and interactions with other components of the liquid, for instance, the blood. However, as outlined before, this may require the channels 120 to comprise a characteristic width or dimension perpendicular to the extension of the channels 120 to be small enough to prevent colloids, blood cells and other larger objects from entering the channels 120. In other words, it may be advisable to implement the channels 120 or pores with a diameter small enough to prevent these larger objects from entering the channels 120. Also the smallness and fewness of the channels serve to control the series resistance in the electrochemical cell and, therefore, prepare the signal for a better read-out.

By providing the control potential to the control electrode 380 ions solute in the drop of liquid will be collected on the walls of the channels 120 being insulated from the control electrode 380 by the insulating region 420. Knowing the control potential with reference to the potential of the counter electrode 160, the amount of electrical charges or ions collected inside the channels can be determined based on the assumption that the channels 120 act like a capacitor. Therefore, by applying a corresponding control potential to the control electrode 380, an ion sensitive enrichment in the cavities 140 can be achieved. As a consequence, the sensor 260 offers the possibility of an additional electrically controllable parameter that may allow an improvement concerning the accuracy of the electrochemical analysis.

The determination of a current or a change of a current may, for instance, be carried out in a pulsed manner. In a first step, the liquid insert the channels may be enriched by applying the corresponding control potential to the control electrode 380. Taking into consideration the dispersion coefficients of the ions in the sample, the control potential should be applied for at least an ion-sensitive amount of time. The measurement electrode 150 may then be brought to the respective voltage with respect to the counter electrode 160 leading to a current pulse, if the voltage or measurement voltage V is only applied for a certain amount of time to the measurement electrode 150.

Naturally, the cyclic voltammetry may also be carried out after selectively enriching the liquid inside the channels 120. Furthermore, the cycles of the cyclic voltammetry may be repeated at different bias potentials or bias voltages applied to the control electrode 380. Therefore, embodiments also comprise a repetitive operation of a sensor device 100 or a sensor 260 according to an embodiment at different bias voltages or bias potentials applied to the control electrode 380 of the electrode active membrane section 130. Accordingly, the coefficient interval may be determined for the ratio of the concentrations of the kinds of ions to be analyzed.

Figure 6:
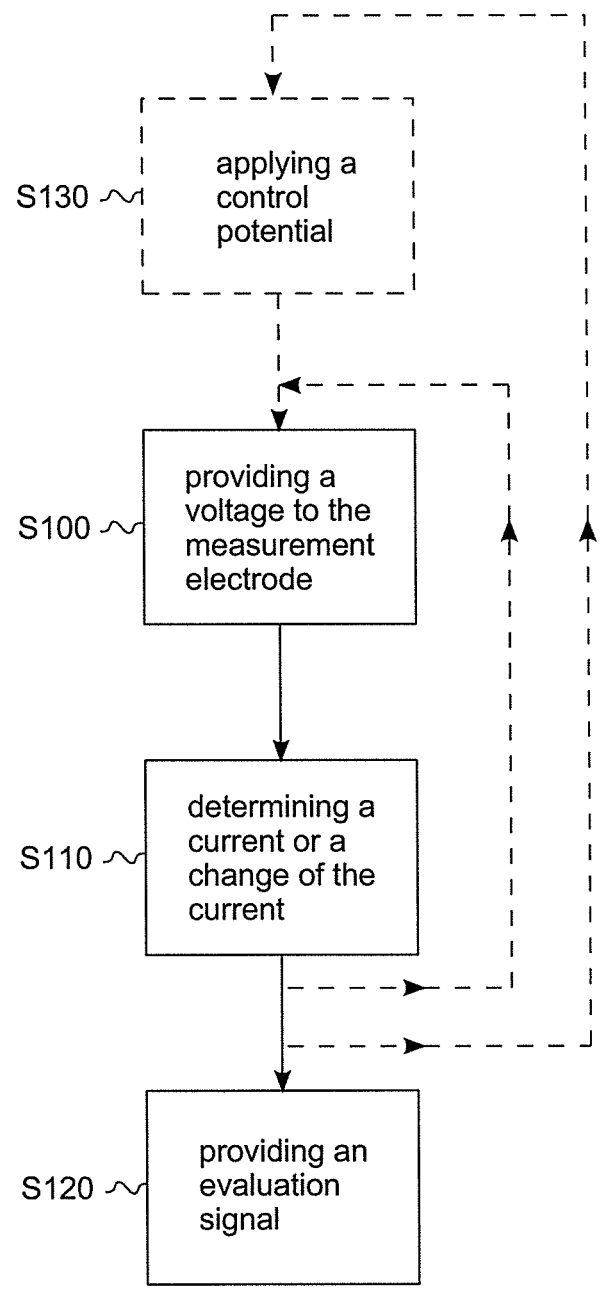
FIG. 6 shows a flow chart of a method according to an embodiment to determine a relative concentration of a first kind of ions with respect to a second kind of ions solute in a drop of liquid.

FIG. 6 shows a flow chart of a method to determine the relative concentration of the first kind of ions with respect to the second kind of ions solute in the drop of liquid. At S100 a voltage is provide to the measurement electrode 150 and the counter electrode 160 as described before. At S110 the current I or the change of the current dI/dV flowing through the drop of liquid in response to the voltage V applied is determined. At S120 an evaluation signal ES indicative of the relative concentration is provided based on the determined current I or the determined change of the current dI/dV.

Optionally, as outlined before, providing the voltage at S100 may also comprise providing a plurality of different voltage values at least one of which is below an electrochemical potential of a first kind of ions, but above an electrochemical potential of the second kind of ions. Moreover, at least one of the different voltage values is above the electrochemical potentials of the first kind of ions and the electrochemical potential of the second kind of ions. Accordingly, determining the current I or the change of the current dI/dV comprises determining a plurality of these values at S110. Accordingly, the evaluation signal ES is provided at S120 based on the plurality of these values determined at 110. To implement such an embodiment, it may be advisable to return after S110 back to S100 as outlined by the dashed line in FIG. 6.

Furthermore, optionally, an embodiment may also comprise applying a control potential at S130, which for instance, may be done before applying the voltage through the measurement electrode 150 and the counter electrode 160 at S100. During this optional act S130, the electrically conductive region 400 forming the control electrode 380 is supplied with a control potential.

Naturally, a method according to an embodiment may further comprise applying a plurality of different control potential values at S130 and, as a consequence, determining a plurality of values of the current I or the change of the current dI/dV at S110. Once again, at 120, providing the evaluation signal ES may be based on the plurality of values determined at S110. Therefore, the method may also comprise returning after S110 to S130 as indicated by the dashed line in FIG. 6.

Naturally, the acts as outlined before may partially or completely be carried out in a timely overlapping manner or completely simultaneously. Moreover, unless explicitly or implicitly excluded, the order of the steps as described in the context of FIG. 6 may also vary.

Embodiments comprise, as outlined before, MEMS-devices for cyclic voltammetry, which are, for instance, applicable to a blood analysis in terms of sodium. The electrochemical single-chip sensor or sensor device 100, which is able to detect or measure a ratio of concentrations of different charge ions with the same polarity in an aqueous or non-aqueous solution comprises the cavity 140 to accommodate the sample volume, typically in the range of microliters. It further comprises an electrode active membrane section 130 capable of filtering macromolecules and larger charged particles. It is also comprises an electrode, which may, for instance, be may a metallic electrode as the measurement electrode 150 for quantitative analysis of ions with a known electrochemical potential as well as a corresponding counter electrode 160, which are comprised in the sensor device 100 either directly on the carrier 170 or on the substrate 110. The sensor device or rather its substrate 110 are electrically coupled via electrical bonds 200, 210 in the embodiments shown in FIGS. 1 to 3, to the same carrier 170. Naturally, also other electrically conducting techniques may be used to electrically couple the substrate 110 and its electrodes to the carrier 170. The sensor device 100 as shown in FIGS. 1 to 3 further comprises a packaging in the form of a protective cover 240 which lies on the opposite side of the funnel 350 and the hole 320 through which the liquid sample can be supplied to the cavity 140.

The substrate 110 with its membrane section 130 comprising the channels 120 is an advantageous aspect, and the control electrode 380 along with its supplementing structures is an option. However, without the membrane section 130 exceeding the electrochemical potential, above which the sodium separation or the potassium separation is thermodynamically possible, a current so high would result such that a significant amount of the ions to be analyzed in the drop of blood would be separated in a single second. Within several milliseconds the concentration of the ions inside the volume of the drop of blood would locally and integrally change significantly. As a consequence, when passing through the characteristics to determine the relative rise of the current I at the different electrochemical voltages with the required precision to distinguish the different proportions may, eventually, not be possible any more.

Using the membrane section 130 allows, therefore, to integrate a defined electrical resistor into the electrolyte to increase the precision of the measurement results by repeatedly passing through the characteristics. In other words, without the membrane section 130 it might not be possible to reliably carry out a cyclic voltammetry measurement since the concentration of the alkaline ions in the drop of blood might change disturbingly. By employing the membrane section 130, it may be possible to allow for such a repeated measurement.

Moreover, the membrane section 130 may be arranged in such a way that it comprises a controlled electrode 380 or a corresponding control terminal. By employing the controlled electrode 380 it may be possible to create at the surface of the channels 120 a capacitor in the membrane section 130 allowing an equilibrium to be achieved between the amounts of sodium and potassium inside the channels 120. As a consequence, by ramping the voltage to analyze the concentration of the respective ions along with the previously described size of the pores or channels 120, it may be possible that the relative portions of potassium and sodium depend less on the differing specific conductivities of these kinds of ions.

To be more precise, the geometry of the membrane section 130 along with its channels 120 may result in a high electrolytic resistance between the drop of blood and the measurement electrode 150 (measurement cathode) and, hence, close down the transport of the ions from the funnel-shaped cavity. The control potential applied to the membrane section 130 may, therefore, determine the ratio of potassium to sodium at the surface of the membrane 130, wherein during the ramping process of the measurement voltage in the vicinity of the cathode, a smaller electrical resistance in the electrolyte may be the result.

With the size of the channels 120 of typically 50 nm to 100 nm, for example, a gate oxide thickness inside the pores or channels 120 of about 10 nm, for example, a fraction of the channels of typically 2% and a thickness of the membrane section 120 of 20 µm, for example, and a control voltage of 1 to 5 V, for example, a ramping of the voltage to analyze the relative concentration of the different kinds of ions can be repeatedly passed through several times within the range of milliseconds. The currents may, for instance, be in the range of 1 µA to 100 µA, without the concentration of the drop of liquid to be analyzed in terms of its ion concentration decreasing in the drop of blood disturbingly.

The description and drawings merely illustrate the principles of the invention. It will thus be appreciated that those skilled in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

Functional blocks denoted as "means for . . . " (performing a certain function) shall be understood as functional blocks comprising circuitry that is adapted for performing or to perform a certain function, respectively. Hence, a "means for s.th." may as well be understood as a "means being adapted or suited for s.th.". A means being adapted for performing a certain function does, hence, not imply that such means necessarily is performing said function (at a given time instant).

The functions of the various elements shown in the FIGS., including any functional blocks labeled as "means", "means for forming", "means for determining" etc., may be provided through the use of dedicated hardware, such as "a former", "a determiner", etc. as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included. Similarly, any switches shown in the FIGS. are conceptual only. Their function may be carried out through the operation of program logic, through dedicated logic, through the interaction of program control and dedicated logic, the particular technique being selectable by the implementer as more specifically understood from the context.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes, which may be substantially represented in computer readable medium and so executed by a computer or processor, whether or not such computer or processor is explicitly shown.

Furthermore, the following claims are hereby incorporated into the Detailed Description, where each claim may stand on its own as a separate embodiment. While each claim may stand on its own as a separate embodiment, it is to be noted that—although a dependent claim may refer in the claims to a specific combination with one or more other claims—other embodiments may also include a combination of the dependent claim with the subject matter of each other dependent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective steps of these methods.

Further, it is to be understood that the disclosure of multiple steps or functions disclosed in the specification or claims may not be construed as to be within the specific order. Therefore, the disclosure of multiple steps or functions will not limit these to a particular order unless such steps or functions are not interchangeable for technical reasons.

Furthermore, in some embodiments a single act may include or may be broken into multiple subacts. Such subacts may be included and part of the disclosure of this single act unless explicitly excluded.

What is claimed is:

1. A sensor device comprising:
    a semiconductor substrate with a membrane, the membrane comprising a plurality of channels, wherein the membrane is configured to accommodate a drop of a liquid at a first side of the membrane;
    a measurement electrode arranged at a second side of the membrane; and
    a counter electrode,
    wherein the measurement electrode and the counter electrode are arranged to allow a voltage to be applied to the drop of liquid;
    wherein the membrane comprises an electrically conductive region and an insulating region abutting the electrically conductive region and the channels, the insulating region arranged in between the electrically conductive region and the channels; and
    wherein the electrically conductive region is configured to apply a control potential to the drop of liquid.

2. The sensor device according to claim 1, wherein the channels comprise a characteristic width of up to 1 µm perpendicular to an extension of the channels between the measurement electrode and a cavity, the channels connecting the cavity and the measurement electrode.

3. The sensor device according to claim 1, wherein the electrically conductive region is configured to apply the control potential to the drop of liquid when such liquid is in a cavity, the channels connecting the cavity and the measurement electrode.

4. The sensor device according to claim 1, wherein the electrically conductive region and the insulating region are configured to apply the control potential to the drop of liquid.

5. The sensor device according to claim 1, wherein the insulating region is formed by at least one of an oxide layer and a nitride layer.

6. The sensor device according to claim 1, wherein the electrically conductive region is formed by a doped region.

7. The sensor device according to claim 1, further comprising a control electrode electrically coupled to the electrically conductive region.

8. The sensor device according to claim 1, wherein the semiconductor substrate is mechanically fixed to a carrier such that a cavity is formed between the plurality of channels of the membrane and the carrier, the channels connecting the cavity and the measurement electrode.

9. The sensor device according to claim 8, wherein the cavity comprises a volume of up to 20 µl.

10. The sensor device according to claim 8, wherein the carrier comprises a hole configured to allow the drop of liquid to be provided to the cavity.

11. The sensor device according to claim 10, further comprising a funnel mechanically fixed around the hole on the carrier on a side facing away from the semiconductor substrate.

12. The sensor device according to claim 8, wherein the counter electrode is provided on the carrier.

13. The sensor device according to claim 8, wherein the carrier comprises a plurality of electrical contacts electrically coupled to the electrodes and configured to electrically connect the electrodes, and wherein the carrier is configured to be mechanically mounted in a holder.

14. A sensor for determining a relative concentration of a first kind of ions with respect to a second kind of ions solute in a drop of a liquid, comprising:
    a semiconductor substrate comprising a plurality of channels;
    a measurement electrode;

a counter electrode, and an evaluation circuit electrically coupled to the measurement electrode and the counter electrode, wherein the measurement electrode and the counter electrode are arranged to accommodate the drop of a liquid and to allow application of a voltage to the drop of liquid;

wherein the plurality of channels is configured to restrict the number of ions reaching the measurement electrode;

wherein the semiconductor substrate comprises an electrically conductive region insulated from the channels by an insulating region abutting the electrically conductive region and the channels, the insulating region arranged in between the electrically conductive region and the channels to collect ions solute in the drop of liquid on the walls of the channels;

wherein the electrically conductive region is configured to apply a control potential to the drop of liquid; and wherein the evaluation circuit is configured to provide the voltage to the measurement electrode and to the counter electrode, determine a current or a change of the current flowing through the drop of liquid in response to the voltage applied, and provide an evaluation signal indicative of the relative concentration based on the determined current or the determined change of the current.

15. The sensor according to claim 14, further comprising a holder configured to mount and unmount the sensor comprising the semiconductor substrate, the measurement electrode, the counter electrode and a plurality of electrical contacts electrically coupled to the electrodes and configured to electrically connect the electrodes, wherein the sensor further comprises a plurality of counter electrical contacts coupled to the evaluation circuit and configured to electrically couple the electrical contacts to the evaluation circuit, when the sensor is mounted to the holder.

16. The sensor according to claim 14, wherein evaluation circuit is configured to provide the voltage comprises providing a plurality of different voltage values, at least one of which is below an electrochemical potential of the first kind of ions, but above an electrochemical potential of the second kind of ions, and at least one of which is above the electrochemical potentials of the first kind of ions and the electrochemical potential of the second kind of ions, wherein the evaluation circuit is further configured to determine the current or the change of current corresponding to one or a plurality of different voltage values, and wherein the evaluation circuit is further configured to provide the evaluation signal based on one or a plurality of values determined in response to the one or plurality of different voltage values.

17. The sensor according to claim 14, wherein the electrically conductive region is configured to apply a control potential to the drop of liquid.

18. The sensor according to claim 17, wherein the evaluation circuit is configured to apply the control potential by applying a plurality of different control potential values to the electrically conductive region, wherein the evaluation circuit is configured to determine the current or the change of the current corresponding to the plurality of different control potential values, and wherein the evaluation circuit is configured to provide the evaluation signal based on the plurality of values determined in response to the plurality of different control potential values.

19. A sensor for determining a relative concentration of $K^+$-ions with respect to $Na^+$-ions solute in a drop of blood, comprising:

a semiconductor substrate with a membrane, the membrane comprising a plurality of channels, wherein the membrane is configured to accommodate a drop of a liquid at a first side of the membrane;

a measurement electrode arranged at a second side of the membrane;

a counter electrode;

a control electrode, and an evaluation circuit electrically coupled to the measurement electrode and the counter electrode, wherein the measurement electrode and the counter electrode are arranged to allow a voltage to be applied to the drop of blood;

wherein the membrane comprises an electrically conductive region and an insulating region abutting the electrically conductive region and the channels, the insulating region arranged in between the electrically conductive region and the channels;

wherein the electrically conductive region is the control electrode and configured to apply a control potential to the drop of liquid; and wherein the evaluation circuit is configured to provide the voltage to the measurement electrode and to the counter electrode, determine a current or a change of the current flowing through the drop of blood in response to the voltage applied, and provide an evaluation signal indicative of the relative concentration based on the determined current or the determined change of the current.

20. The sensor device according to claim 1, further comprising an evaluation circuit electrically coupled to the measurement electrode and the counter electrode, wherein the drop of liquid comprises a first kind of ions and a second kind of ions solute in the drop of a liquid, and wherein the evaluation circuit is configured to provide the voltage to the measurement electrode and to the counter electrode, determine a current or a change of the current flowing through the drop of liquid in response to the voltage applied, and provide an evaluation signal indicative of the relative concentration based on the determined current or the determined change of the current.

21. The sensor according to claim 19, wherein the channels comprise a characteristic width of up to 1 μm perpendicular to an extension of the channels between the measurement electrode and a cavity, the channels connecting the cavity and the measurement electrode.

22. The sensor according to claim 19, wherein the insulating region is formed by at least one of an oxide layer and a nitride layer.

23. The sensor according to claim 19, wherein the semiconductor substrate is mechanically fixed to a carrier such that a cavity is formed between the plurality of channels of the membrane and the carrier, the channels connecting the cavity and the measurement electrode.

24. The sensor according to claim 23, wherein the carrier comprises a hole configured to allow the drop of liquid to be provided to the cavity.

* * * * *